United States Patent

Kemmochi et al.

Patent Number: 5,877,027
Date of Patent: Mar. 2, 1999

[54] METHOD FOR THE ANALYSIS OF IMPURITY CONTENTS IN SILICON DIOXIDE

[75] Inventors: Katsuhiko Kemmochi, Kouriyama; Kiyotaka Maekawa; Chuzaemon Tsuji, both of Takefu; Manabu Saitou, Sabae; Hiroyuki Miyazawa, Takefu; Hiroyuki Watanabe, Takefu, all of Japan

[73] Assignee: Shin-Etsu Quartz Products Co., Ltd., Tokyo, Japan

[21] Appl. No.: 918,133

[22] Filed: Aug. 27, 1997

[51] Int. Cl.$^6$ ........................................................ G01N 1/00
[52] U.S. Cl. ............................ 436/175; 436/83; 436/127; 436/149; 436/150; 436/151; 436/111; 438/14; 134/2; 134/3; 134/10; 134/13; 134/26; 134/28; 134/29
[58] Field of Search .............................. 436/83, 127, 171, 436/175, 149–151; 438/14; 134/2, 3, 10, 13, 26, 28, 29

[56] References Cited

U.S. PATENT DOCUMENTS 5,063,179  11/1991  Menashi et al. ........................ 501/12

FOREIGN PATENT DOCUMENTS

| 0763735 | 3/1997 | European Pat. Off. . |
| 07-72056 | 3/1995 | Japan . |
| 8-145858 | 6/1996 | Japan . |
| 9-257669 | 10/1997 | Japan . |

OTHER PUBLICATIONS

Loon et al "The Determination of Yttrium, Europium, Terbium, Dysprosium, Holmium, Erbium, Tholium, Ytterbium, and Lutetium in Minerals by Atomic–absorption spectrophotomery" Analyst, Jan. 1971, vol. 96, pp. 47–50.

Tong S et al Determination of trace impurities at the pph level in fused silica by spark source mass spectrometry Anal. Chem. Acta (1976) 84 (2) 327–33.

Sulcek et al. "Analytical fast methods for determination of metals and inorganic raw materials XVII. Separation of zirconium or silica gel and its determination in silicates" Collect. Czech. Chem. Common. (1969), 34 (6) 1720–30.

Kiriyama, et al T. Anim–exchange separation and spectro photomatric determination of zirconium and uranium in silicate rocks w/arseno II Nippon Kagaku Katshi (1979) (11) 1609–11. Abstract only.

*Primary Examiner*—Jill Warden
*Assistant Examiner*—S. Carrillo
*Attorney, Agent, or Firm*—Nikaido, Marmelstein, Murray & Oram LLP

[57] ABSTRACT

An analytical method for the quantitative determination of the impurities in silicon dioxide by which trace amounts of hardly soluble impurities contained in silicon dioxide can be reliably decomposed and converted into a solution so that the contents of all of the impurities contained in silicon dioxide or, in particular, zirconium in a natural quartz powder can be accurately determined. Silicon dioxide is decomposed with hydrofluoric acid or an acid mixture of hydrofluoric acid and another inorganic acid to give a decomposition solution which is, as such or after admixture with another inorganic acid, subjected to evaporation to dryness and the residue is heated to cause fusion with addition of a salt or hydroxide of an alkali metal followed by dissolution of the salt or hydroxide of an alkali metal with pure water or with an aqueous solution of an inorganic acid to give an aqueous solution which is subjected to quantitative analysis of the impurities therein.

15 Claims, No Drawings

METHOD FOR THE ANALYSIS OF IMPURITY CONTENTS IN SILICON DIOXIDE

BACKGROUND OF THE INVENTION

1. Field of the Invention

The present invention relates to a method for the analysis of impurity elements in quartz glass used in the fields of semiconductor industries and optical communication or in amorphous or crystalline silicon dioxide as the starting material thereof and, more particularly, relates to a method for the quantitative analysis of the element of zirconium in natural quartz.

2. Description of the Related Art

Heretofore, analysis of the impurity elements in silicon dioxide is conducted for the quantitative analysis by the method in which silicon dioxide is decomposed with hydrofluoric acid and converted into a solution and the impurity elements in this solution are analyzed by the conventional procedure of purity analysis of a solution so as to utilize the results for the calculation of the contents of the impurity elements.

Although hydrofluoric acid has a strong power to decompose silicon dioxide, the dissolving power thereof for other metallic impurities is not always high enough so that it is widely performed in conducting the decomposition to use an acid mixture thereof with nitric acid which has a high dissolving power for metallic elements.

When it is desired to conduct analysis of an element which is subject to vaporization and dissipation in the form of a fluoride, such as boron and the like, it is also performed to add a non-volatile acid such as phosphoric acid and sulfuric acid or to add an organic additive such as mannitol capable of adsorbing and immobilizing the element.

The inventors, however, have discovered the fact that no accurate analytical results can be obtained by these conventional procedures for several of the elements in quartz glass. In particular, it has been found that no accurate quantitative analysis can be performed for the element of zirconium because this element cannot be fully converted into a solution in the course of the starting decomposition procedure of the sample.

Further, the inventors have conducted studies on an efficient means by which this undissolvable matter can be decomposed and converted into a solution and, as a result of the extensively continued investigations for the analytical method by which accurate analysis can be performed for the total amount of the impurities contained therein, have arrived at a discovery that a possibility can be obtained for the analysis of the elements such as zirconium which cannot be accurately analyzed by the conventional analytical methods for quartz glass leading to completion of the present invention.

In particular, natural quartz powders contain impurities in various forms depending on the process of geological formation thereof. It has become clear that a part of them cannot be accurately analyzed by the conventional procedures because they cannot be decomposed and converted into a solution. Moreover, it has also become clear that some of the purification procedures for the purification of the starting materials thereof cause conversion of the existing impurities into a hardly decomposable form.

With the foregoing drawbacks in view, an object of the present invention is to provide a method for the analysis of the amounts of impurities in silicon dioxide by which the total amount of the impurities contained in silicon dioxide or, in particular, zirconium in a natural quartz powder can be quantitatively determined with high accuracy.

SUMMARY OF THE INVENTION

To attain the above mentioned object, the method of the present invention for the analysis of the amount of impurities in silicon dioxide is characterized in that silicon dioxide is decomposed with hydrofluoric acid or an acid mixture of hydrofluoric acid and another inorganic acid, the decomposition solution is subjected to evaporation to dryness either as such or after further admixture of another inorganic acid, the evaporation residue is heated and fused with addition of a salt or hydroxide of an alkali metal, the salt or hydroxide of the alkali metal is dissolved in an aqueous solution of an inorganic acid or in pure water and the solution is subjected to quantitative analysis of the impurities therein.

In a preferable method for the decomposition of silicon dioxide, a solid of silicon dioxide is put in a vessel of, for example, platinum having a dense and smooth surface and hydrofluoric acid, nitric acid and a small amount of sulfuric acid are added thereto to effect decomposition by heating.

If this procedure is conducted under an open condition, the amount of hydrofluoric acid required for the decomposition is four to five times the equivalent amount because not all of the amount of hydrofluoric acid added can be utilized for the decomposition but an advantage is obtained thereby that the treatment can be performed throughout in a platinum vessel having a smooth surface and the alkali fusion can be performed in one and the same vessel without changing it so that the material therein under analysis need not be transferred into another vessel therefor. Needless to say, the environment for the analysis must have appropriate cleanness because decomposition and evaporation to dryness are conducted in an open system.

An alternative particular method for the decomposition and conversion into a solution is that a solid of silicon dioxide is decomposed and converted into a solution by heating at a temperature of 100° C. or higher in a pressurizable acid-decomposition vessel together with hydrofluoric acid. Since the decomposition is conducted in a closed system, an advantage is obtained that no particular control is required for the environmental cleanness and a decomposition solution having a high impurity concentration as desired can be obtained because the decomposition is complete with an approximately equivalent amount of hydrofluoric acid. This method is advantageous when the solution is to be analyzed as such by the flameless atomic absorption spectrophotometric method and also advantageous when the decomposition solution is vaporized to dryness for analysis because the volume of the solution is so small. This method is utilized in conventional methods for the analysis of silicon dioxide by virtue of these two advantages.

On the assumption that the impurities which cannot be analyzed in the conventional method are in the form of fine particles before fusion, the present invention has been completed after examination of this assumption. Accordingly, pressurizable acid-decomposition vessels of polytetrafluoroethylene (PTFE) resin widely used in conventional analytical procedures are not quite satisfactory in this case because such a vessel has microscopic ruggedness on the surface. In particular, a pressurizable acid-decomposition vessel prepared by shaving out from a block of PTFE resin may involve a problem that impurity particles are captured and immobilized in the cavities on the surface of the vessel so that utmost care must be taken when the decomposition solution is to be transferred from a PTFE vessel to a platinum vessel. It is advisable that a platinum crucible is used as an inner vessel in the pressurizable acid-decomposition vessel for the improvement thereof.

In the next place, the solution containing the fluorosilicic acid (hexafluorosilicic acid) is heated under an open condition so that the fluorosilicic acid and silicon fluoride having vaporizability are evaporated and dissipated to the open atmosphere and the residue left after evaporation containing the impurities is free from siliceous constituents.

In the analytical chemistry, the term of "evaporation to dryness" not always means a procedure of conversion into a solid. It is sometimes the case that a sample dried up until it is converted into a solid is no longer recoverable in the subsequent step with a diluted acid. Since the object of the treatment of evaporation to dryness is to have any vaporizable materials completely evaporated and dissipated, the term of "evaporation to dryness" is also applied to the procedure in which a small amount of sulfuric acid as a non-vaporizable acid is added to the sample and heating is continued until rising of a white fume of the sulfuric acid.

In particular, such a procedure is sometimes called "evaporation to dryness with white fuming". In the inventive method, silicon as the principal constituent and fluorine can be completely removed by the addition of sulfuric acid and by conducting evaporation to dryness with white fuming. As the acid to be added in conducting evaporation to dryness with white fuming, not only sulfuric acid but also nitric acid and perchloric acid can be used.

In the present invention, the vaporization treatment to dryness is followed by alkali fusion of the residue. The procedure of "alkali fusion" is a procedure in which a compound such as an alkali metal salt not in the form of an aqueous solution is fused by heating at a temperature of several hundreds °C. or higher into a melt having a strong dissolving power in which the subject substance is dissolved.

In particular, for example, borax or sodium tetraborate as an anhydrous salt thereof as an alkali metal salt is fused by heating at a temperature of 800° C. or higher in a platinum vessel. Sodium tetraborate having no water of crystallization ($Na_2B_4O_7$) is preferable in respect of availability as a high-purity reagent and is more convenient due to the absence of troubles by splashing eventually caused in the elimination of the water of crystallization. Other alkaline compounds such as NaCl, NaOH and the like can be utilized equally.

Platinum-made vessels can be satisfactorily used as the vessel for alkali fusion. Since heating must be conducted at a temperature of 800° C. or higher, resins such as polytetrafluoroethylene cannot be used also in respect of the fine protrusions and cavities found on the inner surface as is mentioned before as well as the heat-resisting property thereof.

An alternative method applicable as the method for the decomposition of silicon dioxide in the method of the present invention is a method in which solid silicon dioxide is decomposed with fluorine vapor. An example of the procedure therefor is described in "Handbook of Analytical Chemistry", revised 4th edition, published by Maruzen Co., 1991, page 764, left column, "b. Silicon Dioxide".

An improvement of this method is disclosed in Japanese Patent Laid-open Publication No.7-72056 and is also useful. In these methods, hydrofluoric acid is taken in a hermetically sealable vessel and solid silicon dioxide is held within the same vessel as being isolated from the acid.

Silicon dioxide is contained, for example, in a small crucible-like vessel. After vaporization and dissipation of the siliceous constituent with the vapor of hydrogen fluoride, the impurities alone are left in the vessel in a dried-up state without any liquid phase. It is a method, in particular, by which the principal constituent of silicon and the impurities are separated without necessitating the procedure of evaporation to dryness.

The dried material obtained by this vapor-phase vapor-decomposition method can be subjected to alkali fusion. It is a preferable method that the silicon dioxide is taken in the first place in a platinum-made vessel to conduct vapor decomposition because particles before fusion are never lost.

The salt after fusion is cooled to room temperature to be converted into a solid alkali salt. This can be dissolved in pure water. Dissolution can be performed more easily by the use of a diluted aqueous solution of an acid such as, for example, diluted hydrochloric acid, diluted nitric acid and the like. It is preferable to conduct heating for the promotion of dissolution to such an extent that boiling does not take place.

The aqueous solution obtained by the above described procedure is adjusted to have a specified volume by a conventional method and subjected to the determination of the impurity concentrations. When analysis is undertaken for zirconium (Zr) which is particularly important in the method of the present invention, ICP-AES (inductively coupled plasma atomic emission spectrometry) can be used satisfactorily.

The samples of silicon dioxide as the objective of the analytical method of the present invention include, in particular, quartz glass, amorphous silica as the base material of quartz glass, natural quartz powders for the preparation of quartz glass articles and so on.

The analytical method of the present invention for zirconium contained in a natural quartz powder is characterized in that the quartz powder is decomposed in a platinum vessel with addition of hydrofluoric acid and sulfuric acid followed by evaporation to dryness until rising of a white fume, the same is admixed with sodium tetraborate and fused by heating at 800° C. or higher followed by dilution with diluted hydrochloric acid after cooling and the element of zirconium in this solution is quantitatively determined by ICP-AES.

The above and other objects, features and advantages of the present invention will become manifest to those skilled in the art on making reference to the following description of preferred embodiments.

DETAILED DESCRIPTION OF THE INVENTION

In the following, the present invention is described in more detail by way of examples although the present invention is never limited thereto in any way.

EXAMPLE 1

A natural quartz powder for the manufacture of quartz glass was taken on a platinum dish in an amount of 5 g and heated thereon with addition of 5 ml of nitric acid, 40 ml of 50% hydrofluoric acid and 2 to 3 drops of sulfuric acid. With additional addition of hydrofluoric acid according to need, the quartz powder was completely decomposed under visual monitoring until it was completely dissolved. With the temperature being further increased, fuming to dryness was conducted until rising of a white fume of sulfuric acid was found.

In this state, 2 g of a powder of sodium tetraborate were added and heated to cause fusion. Heating to 800° C. or higher was required here. After full fusion and cooling by standing, the solid material was dissolved by the addition of 10 ml of a diluted hydrochloric acid prepared by 1:1 dilution. After addition of another 10 ml portion of the diluted hydrochloric acid, the solution was transferred into a flask of 50 ml capacity to make up a specified volume.

The thus obtained sample solution was analyzed by the analytical procedure using the conventional ICP-AES. Table 1 below shows the analytical value of zirconium (Zr) in the natural quartz powder obtained in this way.

EXAMPLE 2

A pressurizable acid-decomposition vessel containing 5 g of a natural quartz powder for the manufacture of quartz glass and 25 ml of 50% hydrofluoric acid was closed and kept under heating at 160° C. for 4 hours to obtain a complete solution as visually examined. This solution was transferred carefully onto a platinum dish and subjected to fuming to dryness with addition of 2 to 3 drops of sulfuric acid until rising of white fume of sulfuric acid was found.

In this state, 2 g of a powder of sodium tetraborate were added and fused by heating. After thorough fusion, the solid material was subjected to fusion with addition of 10 ml of a 1:1 diluted hydrochloric acid. After addition of another 10 ml portion of the diluted hydrochloric acid, the solution was transferred into a 50 ml flask to make up a specified volume.

The sample solution obtained in this way was subjected to analysis by using the conventional ICP-AES to determine the concentrations of impurities in the solid silicon dioxide. Table 1 shows the analytical value of zirconium (Zr) in the natural quartz powder obtained in this manner.

It is important that care is taken in the transfer of the decomposition solution from the pressurizable acid-decomposition vessel to the platinum dish not to leave any invisible undissolved particles because otherwise the analytical value thus obtained may contain a negative error to be lower than the true value though in rare cases.

EXAMPLE 3

Analysis was conducted in the same manner as in Example 1 for the content of zirconium (Zr) in quartz glass prepared from a natural quartz powder to give the results shown in Table 1.

COMPARATIVE EXAMPLE 1

An experiment was conducted in the same manner as in Example 1 excepting for the following points. In the procedure of Example 1, the fuming treatment to dryness was conducted until rising of a white fume of sulfuric acid followed by standing for cooling without undertaking the alkali fusion. After cooling by standing, 20 ml of a 1:1 diluted hydrochloric acid were added and the thus diluted solution was transferred into a 50 ml flask to make up a specified volume.

The sample solution obtained in this way is subjected to analysis by using the conventional ICP-AES to determine the concentrations of impurities in the solid silicon dioxide. Table 1 shows the analytical value of zirconium (Zr) in the natural quartz powder obtained in this manner.

COMPARATIVE EXAMPLE 2

In the same manner as in Example 2, a pressurizable acid-decomposition vessel containing 5 g of a natural quartz powder for the manufacture of quartz glass and 25 ml of 50% hydrofluoric acid was closed and kept under heating at 160° C. for 4 hours to obtain a complete solution as visually examined. This solution was transferred carefully onto a platinum dish and subjected to fuming to dryness with addition of 2 to 3 drops of sulfuric acid until rising of white fume of sulfuric acid was found.

After cooling, 20 ml of a 1:1 diluted hydrochloric acid were added and the thus diluted solution was transferred into a 50 ml flask to make up a specified volume. The sample solution obtained in this way was subjected to analysis by using the conventional ICP-AES to determine the concentrations of impurities in the solid silicon dioxide. Table 1 shows the analytical value of zirconium (Zr) in the natural quartz powder obtained in this manner. Even when this analytical procedure was repeated many times, the analytical results were approximately identical with that shown in the table never to give the high value as obtained by the analytical method of the present invention.

COMPARATIVE EXAMPLE 3

Taking quartz glass as the sample for analysis, analysis for zirconium (Zr) contained therein was undertaken in the same manner as in Example 3. Analysis was conducted in a procedure that alkali fusion was omitted to follow the decomposition in the same manner as in Comparative Example 1. The thus determined content of zirconium (Zr) is shown in Table 1.

According to the analytical method of the present invention, as is understood from Table 1, it has been found that a possibility is obtained for the accurate quantitative determination of the elements such as zirconium (Zr) contained in a quartz powder by virtue of the completeness of conversion into a solution. As is understood from Table 1, it has also been found that accurate overall contents can be obtained for zirconium (Zr) contained in quartz glass.

TABLE 1

|  | Sample | Decomposition method | Decomposition vessel | Alkali fusion | Zr found |
| --- | --- | --- | --- | --- | --- |
| Example 1 | Natural quartz powder | Hot-acid decomposition without pressure | Platinum dish | Yes | 0.7 ppm |
| Example 2 | Natural quartz powder | Acid decomposition under pressure | Teflon | Yes | 0.7 ppm |
| Example 3 | Quartz glass | Hot-acid decomposition | Platinum dish | Yes | 0.7 ppm |

TABLE 1-continued

|  | Sample | Decomposition method | Decomposition vessel | Alkali fusion | Zr found |
|---|---|---|---|---|---|
| Comparative Example 1 | Natural quartz powder | without pressure Hot-acid decomposition without pressure | Platinum dish | No | 0.1 ppm |
| Comparative Example 2 | Natural quartz powder | Acid decomposition under pressure | Teflon | No | 0.1 ppm |
| Comparative Example 3 | Quartz glass | Hot-acid decomposition pressure | Platinum dish | No | 0.6 ppm |

The value of Zr for Example 2 given in Table 1 is a result obtained by repeating the analytical procedure which in few cases gave a low value of about 0. 1 ppm to 0.2 ppm. The unit of Zr given in the table is ppm by weight.

The above given Examples are described for the determination of the content of zirconium (Zr) in a quartz powder, i.e. crystline silicon dioxide, and natural quartz glass, i.e. amorphous silicon dioxide, but the present invention is not limited to these Examples. For example, the method of the present invention is applicable to synthetic quartz crystals and synthetic quartz glass. Besides zirconium (Zr), the method of the present invention can be satisfactorily applied to those elements which form hardly soluble particles such as hafnium (Hf) and the like.

As is described above, a great advantage is obtained according to the present invention that trace amounts of hardly soluble impurities contained in silicon dioxide can be reliably and completely decomposed and converted into a solution so that all of the impurities contained therein or, in particular, zirconium in a natural quartz powder can be quantitatively determined with high accuracy.

Obviously various minor changes and modifications of the present invention are possible in the light of the above teaching. It is therefore to be understood that within the scope of the appended claims the invention may be practiced otherwise than as specifically described.

What is claimed is:

1. A method for analysis of at least one impurity content in silicon dioxide comprising the steps of:
    (a) decomposing silicon dioxide with hydrofluoric acid or an acid mixture of hydrofluoric acid and a first inorganic acid to produce a decomposition solution;
    (b) evaporating to dryness said decomposition solution of step (a) or said decomposition solution after further admixture with a second inorganic acid, wherein said evaporating to dryness produces a residue;
    (c) adding a salt or a hydroxide of an alkali metal to said residue;
    (d) heating said residue to effect fusion of said residue with said salt or said hydroxide of said alkali metal;
    (e) dissolving said salt or said hydroxide of said alkali metal in water or in a first aqueous solution of a third inorganic acid to produce a second aqueous solution; and
    (f) subjecting said second aqueous solution to quantitative analysis, to determine said at least one impurity content in said silicon dioxide.

2. The method for the analysis of said at least one impurity content in silicon dioxide according to claim 1, wherein the silicon dioxide is selected from the group consisting of quartz glass, silica used in the manufacture of quartz glass and a natural quartz powder used in the manufacture of quartz glass.

3. The method for the analysis of said at least one impurity content in silicon dioxide according to claim 1, wherein the impurity in the silicon dioxide is zirconium.

4. The method for the analysis of said at least one impurity content in silicon dioxide according to claim 2, wherein the impurity in the silicon dioxide is zirconium.

5. The method for the analysis of said at least one impurity content in silicon dioxide according to claim 1, wherein the decomposition solution is further admixed with said second inorganic acid comprising sulfuric acid and subjected to said evaporation to dryness to produce a rising of white fume.

6. The method for the analysis of said at least one impurity content in silicon dioxide according to claim 2, wherein the decomposition solution is further admixed with said second inorganic acid comprising sulfuric acid and subjected to said evaporation to dryness to produce a rising of white fume.

7. The method for the analysis of said at least one impurity content in silicon dioxide according to claim 3, wherein the decomposition solution is further admixed with said second inorganic acid comprising sulfuric acid and subjected to said evaporation to dryness to produce a rising of white fume.

8. The method for the analysis of said at least one impurity content in silicon dioxide according to claim 1, wherein said step of decomposing silicon dioxide is conducted in a platinum vessel.

9. The method for the analysis of said at least one impurity content in silicon dioxide according to claim 2, wherein said step of decomposing silicon dioxide is conducted in a platinum vessel.

10. The method for the analysis of said at least one impurity content in silicon dioxide according to claim 3, wherein said step of decomposing silicon dioxide is conducted in a platinum vessel.

11. The method for the analysis of said at least one impurity content in silicon dioxide according to claim 4, wherein said step of decomposing silicon dioxide is conducted in a platinum vessel.

12. A method for the analysis of zirconium in quartz powder, comprising the steps of:
    (a) decomposing the quartz powder in a platinum vessel with addition of hydrofluoric acid and sulfuric acid followed by evaporation to dryness until rising of white fume, thereby producing a decomposition solution;
    (b) adding sodium tetraborate to said decomposition solution to produce a first mixture;
    (c) heating said first mixture at a temperature of 800° C. or higher;

(d) cooling said first mixture;

(e) diluting said first mixture with diluted hydrochloric acid to produce a diluted solution; and (f) determining quantitatively said zirconium in said diluted solution by inductively coupled plasma atomic emission spectrometry.

13. The method for the analysis of said at least one impurity content in silicon dioxide according to claim 1, wherein the salt of said alkali metal comprises borax or sodium tetraborate, and said heating step (d) is conducted at a temperature of 800° C. or higher.

14. The method for the analysis of said at least one impurity content in silicon dioxide according to claim 2, wherein the salt of said alkali metal comprising borax or sodium tetraborate is fused by heating at a temperature of 800° C. or higher.

15. The method for the analysis of said at least impurity content in silicon dioxide according to claim 3, wherein the salt of said alkali metal comprising borax or sodium tetraborate is fused by heating at a temperature of 800° C. or higher.

* * * * *